United States Patent [19]

Kanamaru et al.

[11] 4,248,892
[45] Feb. 3, 1981

[54] ANTIFIBROTIC AGENT

[75] Inventors: Tsuneo Kanamaru, Takatsuki; Takenori Ishimaru, Suita; Hisayoshi Okazaki, Kyoto, all of Japan

[73] Assignee: Takeda Chemical Industries, Ltd., Osaka, Japan

[21] Appl. No.: 46,632

[22] Filed: Jun. 7, 1979

[30] Foreign Application Priority Data

Jun. 9, 1978 [JP] Japan ................................ 53/70159

[51] Int. Cl.$^3$ .............................................. A61K 31/19
[52] U.S. Cl. .................................................... 424/317
[58] Field of Search .......................................... 424/317

[56] References Cited
PUBLICATIONS

Chemical Abstracts, vol. 38:5319, 1944, vol. 49, 11174e (1955).

Primary Examiner—Frederick E. Waddell
Attorney, Agent, or Firm—Wenderoth, Lind & Ponack

[57] ABSTRACT

Compounds of the formula

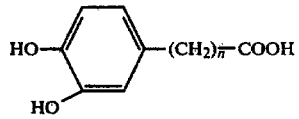

wherein n is equal to zero or 1 and their physiologically acceptable salts are effective for the prophylaxis or treatment of the fibrosis due to excessive collagen accumulation in mammal.

7 Claims, No Drawings

ANTIFIBROTIC AGENT

The present invention relates to a drug for the prophylaxis or treatment of fibrosis in mammals.

Recent years have witnessed a heightened attention to abnormal deposition or structural alteration of collagen and a series of diseases with the resultant functional disorders or organs, e.g. various fibrosis, particularly hepatic cirrhosis, pulmonary fibrosis and arterioscrelosis, as well as various kinds of collagen disease. Accordingly, the development of drugs effective for the suppression of fibrosis has been demanded. The intensive research undertaken in an attempt to develop a new and effective medicine for the inhibition of abnormal deposition of collagen led us to the finding that the compounds represented by the formula;

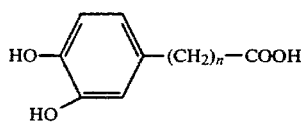

wherein n is equal to zero or 1 or its physiologically acceptable salt have a potent inhibitory action on protocollagen prolyl hydroxylase which is considered to be one of the rate-limiting enzymes in the biosynthesis of collagen, and are able to specifically inhibit the biosynthesis of collagen and that, therefore, these compounds are of value as drugs for the prophylaxis and treatment of fibrosis arising from an excessive accumulation of collagen. The above findings have resulted in the development of an antifibrotic agent of this invention.

The above formula (I) encompasses two compounds, that is to say, protocatechuic acid (n is equal to 0) and homoprotocatechuic acid (n is 1), both of which are known compounds ["The Dictionary of Organic Compounds", p.p. 1056 & 1100, Eyre and Spottiswood, Great Britain (1965)]. The compound (I) may be used in the form of salts with physiologically acceptable bases such as alkali metals (sodium, potassium, etc.), and alkaline earth metals (calcium, etc.) or ammonium.

To establish the utility of compound (I) according to this invention as antifibrotic agent, the activity of inhibiting protocollagen prolyl hydroxylase, that of inhibiting collagen biosynthesis in normal rats and in hepatocirrhotic rats, as well as the pertinent assay procedures, will be described in Example 1 hereinafter.

The compound (I) and physiologically acceptable salts thereof are used for the prophylaxis and treatment of fibrosis of tissues in mammals (such as laboratory animals, e.g. rabbit, rat, mouse, etc.; pet animals, e.g. dog, cat, etc.; and human beings).

Fibrosis is a generic name designating all the diseases due to excessive accumulation of collagen. Thus, for example, it may mean any and all of pulmonary fibrosis, hepatic cirrhosis, renal sclerosis, arteriosclerosis, scleroderma, myelofibrosis, rheumatoid arthritis, etc. [Hotchi: Naika (Internal Medicine, Tokyo) 41, 724 (1978)].

When the compound (I) or salt thereof is used for the prevention or treatment of the above-mentioned fibrosis, it can safely be orally or parenterally administered, either as it is or as formulated with an appropriate carrier, vehicle or diluent, in such dosage forms as powders, granules, tablets, capsules, injections, etc. Each dosage unit generally contains 50 mg to 500 mg of the compound (I). While the proper dosage depends on such factors as the disease to be managed, condition, subject and route of administration, it is preferably 5 mg/kg to 100 mg/kg body weight per day for oral route. For instance about 300 mg to 3,000 mg daily are advantageously given in 1 to 3 divided portions, by the oral route when the disease is hepatic cirrhosis, arteriosclerosis or rheumatoid arthritis in an adult human.

The following Examples are merely for illustrative purposes and are not to be construed as limitations of the present invention.

Throughout the foregoing description as well as in the following, Examples and Claims, "$\mu$g", "mg", "g", "ml", "l" and "$\mu$ mol" respectively refer to "microgram(s)", "milligram(s)", "gram(s)", "milliliter(s)", "liter(s)" and "micromol(s)".

EXAMPLE 1

(1) Activity to inhibit protocollagen prolyl hydroxylase

Method for the preparation of protocollagen prolyl hydroxylase: The method of K.I. Kivirikko et al and that of J. Halme et al were partially modified. [cf. Journal of Biological Chemistry 242, 4007 (1967) and Biochimica et Biophysica Acta 198, 460 (1970)]. Thus, 190 chick embryos (14 days old) were homogenized in 1600 ml of NaCl-GlycineTris{tris(hydroxymethyl)aminomethane}-HCl buffer containing 0.1% Triton [polyethylene glycol p-isooctylphenyl ether] X-100 (pH 7.5) and centrifuged. To 2,350 ml of the supernatant was added ammonium sulfate, and the fractions corresponding to 15 through 50% ammonium sulfate saturation were collected, dissolved in the same buffer as above, dialyzed against the same buffer and precipitated by the addition of calcium phosphate gel to the internal solution. From the precipitate, the enzyme was extracted out with phosphate buffer (pH 7.0). The extract was run onto a column of DEAE[diethylaminoethylether]-cellulose and fractional elution was carried out with NaCl-Glycine-TrisHCl buffer. The enzyme-rich fractions amounting to 740 ml were pooled and frozen for later use.

Procedures for the determination of enzyme activity and inhibitory activity: The method of Y. Kikuchi et al [Biochemical Journal 115, 569(1969)] was generally followed using (Pro-Pro-Gly)$_5$.4H$_2$O [(Proline-Proline-Glycine)$_5$.4H$_2$O] (Protein Research Foundation, Osaka, Japan Code No. 4005) as the substrate.

Thus, 1.5 ml of a reaction mixture containing 50 $\mu$mols of Tris-HCl buffer (pH 7.8), 0.1 $\mu$mol of 1-$^{14}$C-$\alpha$-ketoglutarate (0.016 $\mu$ Ci), 0.5 $\mu$mol of ascorbate, 0.1 $\mu$mol of ferrous ammonium sulfate, 4.0 mg of heat denatured bovine serum albumin, 0.1 mg of crystalline bovine liver catalase, 0.15 $\mu$mol of dithiothreitol, 0.15 mg of (Pro-Pro-Gly)$_5$.4H$_2$O, 0.5 ml of the enzyme solution and 0.1 ml of either methanol or methanol solution containing an inhibitor was put in a sealed test tube in which a filter paper impregnated with Hyamine (Hydroxide and Hyamine 10-X (Packard Instrument Co.)] had been hung and the reaction was carried out under shaking at 37° C. for 30 minutes. The reaction was terminated by the addition of 0.5 ml of 25% trichloroacetic acid and the enzymic activity was determined by measuring the radioactivity of the released $^{14}$CO$_2$ trapped in filterpaper. The inhibitory activity of each compound (I) is shown as the concentration (ID$_{50}$) of the compound which was required for a 50% inhibition of the enzymic activity in the absence of the inhibitor.

The ID$_{50}$ values of the compounds with respect to protocollagen prolyl hydroxylase are given in Table 1.

Table 1

| Compound | ID$_{50}$ (µg/ml) |
| --- | --- |
| Protocatechuic acid | 3 |
| Homoprotocatechnic acid | 3 |

(2) Inhibition of collagen biosynthesis in normal rats

According to the partially modified method of R.A. Salvador et al [Archives of Biochemistry and Biophysics 174, 382 (1976)], the following experiment was carried out with SD rats (female, 3 weeks old) in groups of 4 animals.

The test compound suspended in 4% gum arabic-physiological saline was intraperitoneally administered to rats in doses of 100 mg/kg at intervals of 24 hours for 6 consecutive days.

During the final 3 days, 5 µg/rat of 17-β-estradiol in 5% ethanol-saline solution or 5% ethanol-saline solution was administered one hour after the administration of compound (I). On the 7th day, each rat was killed and the uterus was excised, washed with ethanol-diethylether, dried at 60° C. for 2 hours and weighted to know the dry weight. The dry preparation was hydrolyzed with 3 ml of 6N-HCl at 110° C. for 22 hours, after which it was concentrated to dryness to remove the hydrochloric acid. The total amino acid in the hydrolyzate was determined by ninhydrin assay and from this value the total protein content of uterus was calculated as leucine equivalent. The amount of hydroxyproline in the hydrolyzate was also measured by the method of Blumenkratz et al [Analytical Biochemistry 63, 331 (1975)] and multiplied by 7.23 to obtain the amount of collagen. The amount of noncollagenous protein was calculated by substracting the amount of collagen from the total amount of protein.

The inhibitory activity of this compound on the synthesis of collagen and noncollagenous protein in the uteri of 17-β-estradiol-stimulated immature rats are shown as % reductions in the amounts of collagen and noncollagenous protein. Inhibition rate is calculated by the equation described in the legend of Table 2. The inhibitory effects of the compound on collagen biosynthesis are shown in Table 2.

Male Sprague-Dawley rats weighting approximately 150 g each were divided into three groups. The first group received both 10% CCl$_4$-olive oil mixture (1 ml/rat) and compound (I) (100 mg/kg) intraperitoneally three times weekly for a total 10 doses. The second and third groups received 10% CCl$_4$-olive oil mixture (1 ml/rat) and olive oil (1 ml/rat) intraperitoneally three times weekly for a total 10 doses, respectively. The rats were sacrificed two days after the last injection and the livers were immediately removed for the assays.

Assay of protocollagen prolyl hydroxylase activity:

A 10% homogenate of the liver was prepared in 20 m mol/l Tris-HCl buffer (pH 7 5) containing 0.2 mol/l NaCl, 0.1 mol/l glycine, $5\times10^{-5}$ mol/l 1,4-dithiothreitol, and 0.1% Triton X-100 using a Polytron homogenizer. The homogenate was centrifuged at 15,000 g for 20 minutes and the clear supernatant was assayed for protocollagen prolyl hydroxylase activity by the method of Hutton et al [Analytical Biochemistry 16, 384 (1966)]. The protein content of the homogenate was measured by the method of Lowry et al [Journal of Biological Chemistry 193, 265 (1951)] using bovine serum albumin as the standard.

Assay of hydroxyproline content:

Hydroxyproline content of the livers was measured in a 6N-HCl hydrolysate (110° C., 22h) by the method of Blumenkrantz et al.

The specific activity of protocollagen prolyl hydroxylase and hydroxyproline content in the liver treated with the compound as shown in Table 3.

Table 3

| Group | Prolyl hydroxylase (dpm*/mg of protein) | Hydroxyproline (µg/mg of liver) |
| --- | --- | --- |
| Control (olive oil) | 472 ± 71 | 0.21 ± 0.02 |
| CCl$_4$ | 2802 ± 250 | 1.08 ± 0.22 |
| CCl$_4$ + protocatechui acid | 1463 ± 236 | 0.70 ± 0.09 |

*decay per minute

From Table 3, it is clear that protocollagen prolyl hydroxylase activity and hydroxyproline content in the livers treated with compound (I) was significantly decreased as compared to those in the livers not treated.

It is thus conjectured that the inhibitory activity of (I) is specific to collagen. The above fact, in turn, indicates that by its inhibition of collagen biosynthesis in animal tissues, the compound (I) is of value in the prophylaxis Table 2

| Dosed groups | Body weight of rats, 7th day (g) | Total protein (mg/uterus) | Total collagen (mg/uterus) | Inhibition rate (%)* | |
| --- | --- | --- | --- | --- | --- |
| | | | | collagen | Noncollagenous protein |
| Control (1) (5% ethanol-saline) | 86 ± 4 | 13.9 ± 1.6 | 3.12 ± 0.48 | — | — |
| Control (2) 17-β-estradiol | 82 ± 4 | 28.6 ± 7.4 | 4.39 ± 0.16 | 0 | 0 |
| 17-β-estradiol + protocatechnic acid | 75 ± 3 | 25.4 ± 2.2 | 3.31 ± 0.37 | 85 | 15 |

*Inhibition rate (%) = $\frac{\text{Value for control (2)} - \text{Value for dosed group}}{\text{Value for control (2)} - \text{Value for control (1)}} \times 100$ It will be apparent, if only from Table 2 above, that despite its sparse inhibition of the biosynthesis of noncollagenous protein, the compound (I) is highly inhibitory to collagen biosynthesis.

(3) Effect of compound (I) on collagen biosynthesis in carbon tetrachloride-induced hepatic cirrhosis Induction of hepatic cirrhosis in rats:

and treatment of fibrosis such as hepatic cirrhosis, caused by an excessive accumulation of collagen.

Acute toxicity

Protocatechuic acid was intraperitoneally administered to male 4-week-old mice in groups of 5 animals and the animals were kept under observation for 8 days. The LD$_{50}$ values thus found was >400 mg/kg for it.

EXAMPLE 2

Typical formulations for compound (I) as a drug for the prophylaxis or treatment of fibrosis are as follows.

1. Tablets 300 mg of protocatechuic acid, 47 mg of lactose, 40 mg of corn starch, 12 mg of hydroxypropyl-cellulose-L and 1 mg of magnesium stearate are admixed and tableted by the established procedure (wet-process).

2. Capsules

| (1) | Homoprotocatechuic acid | 300 mg |
| --- | --- | --- |
| (2) | Lactose | 135 mg |
| (3) | Corn starch | 60 mg |
| (4) | Magnesium stearate | 5 mg |
|     |                     | 500 mg per capsule |

(1), (2), (3) and half of (4) are admixed and granulated. Then, the remaining half of (4) is added and the entire composition was sealed into a No. 1 gelatin capsule (Japanese Pharmacopoeia, 8th Rev.).

3. Capsules

| (1) | Sodium protocatechuate | 350 g |
| --- | --- | --- |
| (2) | Corn starch | 700 g |
| (3) | Talcum | 75 g |

All the components are intimately mixed and used in filling 1,000 gelatin capsules, each filled capsule containing 350 mg of the active ingredient (1).

What is claimed is:

1. A method for the prophylaxis or treatment of fibrosis due to excessive collagen accumulation in mammal, which comprises administering to mammal an effective amount of a compound of the formula

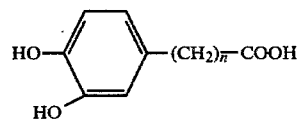

wherein n is equal to zero or 1, or its physiologically acceptable salt.

2. A method according to claim 1, wherein n is equal to zero, namely the compound is protocatechuic acid.

3. A method according to claim 1, wherein the fibrosis is pulmonary fibrosis, hepatic cirrhosis, renal sclerosis, arteriosclerosis, scleroderma or rheumatoid arthritis.

4. A method according to claim 3, wherein the fibrosis is pulmonary fibrosis.

5. A method according to claim 3, wherein the fibrosis is hepatic cirrhosis.

6. A method according to claim 1, wherein the compound or its physiologically acceptable salt is orally administered.

7. A method according to claim 6, wherein the compound or its physiologically acceptable salt is administered at the dose level of 5 mg/kg to 100 mg/kg body weight per day.